(12) United States Patent
Heimann et al.

(10) Patent No.: US 6,414,191 B1
(45) Date of Patent: Jul. 2, 2002

(54) METHOD FOR THE CONTINUOUS PRODUCTION OF METHOXYAMINE HYDROCHLORIDE

(75) Inventors: Frank Heimann, Ludwigshafen; Werner Peschel, Freinsheim; Bernd Bartenbach, Limburgerhof; Horst Hartmann, Böhl-Iggelheim; Michael Keil, Freinsheim; Josef Wahl, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,351

(22) PCT Filed: Feb. 28, 2000

(86) PCT No.: PCT/EP00/01638

§ 371 (c)(1),
(2), (4) Date: Sep. 11, 2001

(87) PCT Pub. No.: WO00/55121

PCT Pub. Date: Sep. 21, 2000

(30) Foreign Application Priority Data

Mar. 15, 1999 (DE) .......................................... 199 11 234

(51) Int. Cl.$^7$ ............................................. C07C 239/20
(52) U.S. Cl. ...................................... 564/296; 564/292
(58) Field of Search .................................. 564/292, 296

(56) References Cited

FOREIGN PATENT DOCUMENTS

EP 0 259 850 * 3/1988 ......... C07C/131/00

OTHER PUBLICATIONS

Database CAPLUS on STN, Acc. No. 1988:492272, Will et al., 'Procedure for the preparation of O–substituted hydroxylamine hydrochlorides, intermediates for phar. and plant protective agents.' EP 259850 (abstract).*

* cited by examiner

Primary Examiner—Brian J. Davis
(74) Attorney, Agent, or Firm—Keil & Weinkauf

(57) ABSTRACT

The present invention relates to a process for the continuous preparation of methoxyamine hydrochloride by cleavage of acetone oxime methyl ether by means of hydrogen chloride and water, wherein the cleavage is carried out in a reaction column having less than 20 theoretical plates and the amount taken off at the top is set to at least 30% of the amount of feed.

3 Claims, No Drawings

METHOD FOR THE CONTINUOUS PRODUCTION OF METHOXYAMINE HYDROCHLORIDE

This is a 371 of PCT/EP00/01638 filed Feb. 28, 2000.

The present invention relates to a process for the continuous preparation of methoxyamine hydrochloride by cleavage of acetone oxime methyl ether by means of hydrogen chloride in the presence of water.

The prior art describes both batchwise processes (EP-A 591 798, EP-A 708 082) and a continuous process (EP-A 259 850) for preparing methoxyamine hydrochloride from acetone oxime methyl ether. The advantages of a continuous process are generally the smaller dimensions of the apparatuses, the higher degree of automation and, in particular, the increased process capability. Industrial products produced using continuous processes are therefore usually more economical than the products obtained from batchwise processes. Furthermore, consistently high product qualities can be achieved by means of continuous processes.

However, the continuous process known from EP-A 259 850 for the cleavage of acetone oxime methyl ether by means of hydrogen chloride to form methoxyamine hydrochloride has the great disadvantage that a reaction column having many theoretical plates is necessary to achieve high yields. Such an apparatus is costly and its operation consumes a large amount of energy.

It is an object of the present invention to develop a continuous process which does not have the disadvantage described in EP-A 259 850.

We have found that this object is achieved by the process mentioned at the outset when the cleavage is carried out in a reaction column having less than 20 theoretical plates and the amount taken off at the top is set to at least 30% of the amount of feed.

The acetone formed in the reaction and excess hydrogen chloride and water are taken off at the top. In the process of the invention, it is important that at least 30% of the amount of feed are taken off at the top, since otherwise the acetone concentration would be too high, especially in the upper segments of the reaction column. A high acetone concentration has an adverse effect on the position of the reaction equilibrium and also leads to a lowering of the internal temperature in these segments. If the cleavage of the acetone oxime methyl ether is carried out in a reaction column having less than 20 theoretical plates and the acetone is not removed to a sufficient extent, the cleavage product methoxyamine hydrochloride is obtained in completely unsatisfactory yields.

The method employed in the process of the present invention in which at least 30% of the amount of feed are taken off at the top leads to a homogeneous temperature distribution over the column. In general, the temperature difference between the bottom and the top (measured on the second-last vertical plate) is less than 15° C. and preferably less than 10° C.

The process of the present invention surprisingly makes it possible to obtain methoxyamine hydrochloride in excellent yields even in a column have less than 20 theoretical plates.

In the process of the present invention, the mixture taken off at the top of the column is preferably taken off at a fixed reflux ratio of from 2 to 15, preferably from 3 to 11. The small number of theoretical plates and the favorable reflux ratio result in a significantly shorter mean residence time of the reaction mixture in the column compared to EP-A 259 850. Surprisingly, excellent yields can be achieved in the process of the present invention despite the short mean residence time of only 20 minutes. Longer residence times in the column are, however, likewise possible.

The process of the invention will be described in more detail below.

The starting compound acetone oxime methyl ether is prepared by methods known from the literature, in particular by the process described in EP-A 708 082.

The cleavage is generally achieved by addition of aqueous hydrochloric acid having a concentration of at least 22%. In particular, the cleavage is carried out in hydrochloric acid having a concentration of from 22 to 38% by weight, preferably from 30 to 38% by weight (concentrated hydrochloric acid). However, the cleavage can also be carried out by passing gaseous hydrogen chloride into the ether. In this case, water is added to the reaction mixture in an amount sufficient to prevent the methoxyamine hydrochloride formed from crystallizing out in the column. In general, 2 molar equivalents of water per mole of acetone oxime methyl ether used are sufficient for this purpose.

The hydrogen chloride introduced in the form of hydrochloric acid or gaseous hydrogen chloride is generally used in an excess over the acetone oxime methyl ether, but is used in at least the stoichiometric amount. The reaction is preferably carried out at a molar ratio of hydrogen chloride to acetone oxime methyl ether of 2:1.

Particular preference is given to using a solution of acetone oxime methyl ether in aqueous hydrochloric acid.

Suitable reaction columns are, in particular, tray columns of all types. Bubble cap tray columns are particularly useful since the residence times on the trays can be readily set in them. Packed columns are also possible. The number of theoretical plates is restricted to 19 for economic reasons. The minimum number of theoretical plates necessary in the column to guarantee complete conversion depends on the reflux ratio set at the top of the column. Since, as mentioned above, a reflux ratio of from 2 to 15 is preferably set, the minimum number of theoretical plates in the reaction column is 8. On the other hand, if a reflux ratio of 16 or more is chosen, acetone oxime methyl ether can be cleaved completely even in reaction columns having less than 8 theoretical plates.

The choice of the tray onto which the feed is introduced is demonstrated by way of example in the examples. It is generally chosen so that at least 60% of the trays or theoretical plates are above the feed point and at least 20% of the trays or theoretical plates are below the feed point. However, deviations can be made from this advantageous condition since the aim of the process can nevertheless be achieved by appropriate selection of the other parameters such as reflux ratio, temperature and amount taken off at the top.

The reaction temperature is generally in the range from 40 to 110° and preferably from 65 to 95° C. and is determined, in particular, by the amount taken off at the top and the pressure which is set. The process is preferably carried out at a pressure of from 100 mbar to 3 bar.

The reactants acetone oxime methyl ether, water and hydrogen chloride or aqueous hydrochloric acid are advantageously fed into the middle section of the column. Feed rate and bottom heating power are generally selected so that the mean residence time in the column is from 20 minutes to 2 hours.

Furthermore, the cleavage can also be carried out in the presence of an inert organic solvent. The solvent is preferably recovered at the top of the column and should therefore have a boiling point of not more than 150° C. If aqueous hydrochloric acid is used for the cleavage, particularly advantageous solvents are those such as toluene which form an azeotrope with aqueous hydrochloric acid.

Methoxyamine hydrochloride is preferably obtained at he bottom of the column in the form of an aqueous suspension or solution which is continuously discharged, and the methoxyamine hydrochloride can be obtained in pure form by, for example, evaporation of the diluent or crystallization. In all steps for the isolation of pure methoxyamine hydrochloride, a temperature of 60° C. should not be exceeded for safety reasons. The aqueous solution of methoxyamine hydrochloride obtained is preferably processed further without isolation of the methoxyamine hydrochloride. The yield is generally >98%.

Methoxyamine hydrochloride is an important intermediate in the preparation of drugs and crop protection agents.

PREPARATION OF METHOXYAMINE HYDROCHLORIDE

EXAMPLE 1

400 g/h of a solution of 26.1% by weight of acetone oxime methyl ether in 31% strength hydrochloric acid were fed continuously into a bubble cap tray column having 15 theoretical plates (corresponding to 25 practical trays) and an internal diameter of 30 mm at the $11^{th}$ practical tray. The column was equipped with a thin film evaporator and an automatic runback divider.

The reflux ratio was fixed at 5. The bottom heating power was selected so that the temperature on the $23^{rd}$ practical tray was >84° C. at a pressure of 450 mbar at the top of the column. The temperature at the bottom of the column was 95° C. In this way, 280 g/h (maximum of 70% of the feed) of an aqueous hydrochloric acid solution of 35.1% by weight of methoxyamine hydrochloride (corresponding to a yield of 98.2%) could be taken off continuously at the bottom. The distillate obtained at the top comprised mainly acetone together with water and dissolved hydrogen chloride.

EXAMPLE 2

500 g/h of a solution of 27.5% by weight of acetone oxime methyl ether in concentrated hydrochloric acid were fed continuously into a bubble cap tray column having 15 theoretical plates (corresponding to 25 practical trays) and an internal diameter of 50 mm at the $11^{th}$ practical tray. The reflux ratio was fixed at 3. The bottom heating power was selected so that the temperature on the 22nd practical tray was >84° C. at a pressure of 450 mbar at the top of the column. The temperature at the bottom of the column was 98° C. In this way, 350 g/h (maximum of 70% of the feed) of an aqueous hydrochloric acid solution of 37.5% by weight of methoxyamine hydrochloride (corresponding to a yield of 99.5%) could be taken off continuously at the bottom. The distillate obtained at the top comprised mainly acetone together with water and dissolved hydrogen chloride.

EXAMPLE 3

The cleavage was carried out in a bubble cap tray column having 9 theoretical plates at a reflux ratio of 11 under conditions otherwise identical to those in Example 1. A result comparable to that of Example 1 was achieved.

EXAMPLE 4 (COMPARATIVE EXAMPLE)

500 g/h of a solution of 29.3% by weight of acetone oxime methyl ether in concentrated hydrochloric acid were fed continuously into a bubble cap tray column having 18 theoretical plates (corresponding to 30 practical trays) and an internal diameter of 50 mm at the $16^{th}$ practical tray. The column was equipped with a thin film evaporator and an automatic runback divider. The reflux ratio was fixed at 4. The bottom heating power was selected so that the temperature on the $28^{th}$ practical tray was >80° C. at a pressure of 450 mbar at the top of the column. The temperature at the bottom of the column was 97° C. In this way, 380 g/h (76% of the feed) of an aqueous hydrochloric acid solution of 32.6% by weight of methoxyamine hydrochloride (corresponding to a yield of 88.1%) could be taken off continuously at the bottom. The distillate obtained at the top comprised mainly acetone together with water and dissolved hydrogen chloride. Appreciable contents of unreacted acetone oxime methyl ether were found in the outputs from the top and bottom (3.4 and 3.5% by weight, respectively).

We claim:

1. A process for the continuous preparation of methoxyamine hydrochloride by cleavage of acetone oxime methyl ether by means of hydrogen chloride and water, wherein the cleavage is carried out in a reaction column having less than 20 theoretical plates and the amount taken off at the top is set to at least 30% of the amount of feed, and hydrogen chloride and water means a hydrochloric acid having a concentration of at least 22% by weight.

2. A process as claimed in claim 1, wherein the hydrogen chloride and water are used in the form of aqueous hydrochloric acid having a concentration of from 22 to 38% by weight.

3. A process as claimed in claim 1, wherein an internal temperature of from 40 to 110° C. is set.

* * * * *